(12) United States Patent
Snyder et al.

(10) Patent No.: US 6,541,255 B1
(45) Date of Patent: *Apr. 1, 2003

(54) ENGRAFTABLE HUMAN NEURAL STEM CELLS

(75) Inventors: Evan Y. Snyder, Jamaica Plain, MA (US); John H. Wolfe, Philadelphia, PA (US); Seung U. Kim, Vancouver (CA)

(73) Assignees: The Children's Medical Center Corporation, Boston, MA (US); The University of British Columbia (CA); The University of Pennsylvania, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/398,297

(22) Filed: Sep. 20, 1999

Related U.S. Application Data

(63) Continuation of application No. 09/133,873, filed on Aug. 14, 1998, now Pat. No. 5,958,767.

(51) Int. Cl.$^7$ ................................................. C12N 5/08
(52) U.S. Cl. .......................................... 435/368; 514/44
(58) Field of Search ................................ 435/368, 455, 435/366, 325; 514/44

(56) References Cited

U.S. PATENT DOCUMENTS

| | | | |
|---|---|---|---|
| 5,624,830 A | 4/1997 | Mullen et al. | 435/456 |
| 5,750,376 A | 5/1998 | Weiss et al. | 435/69.52 |
| 5,753,506 A | 5/1998 | Johe | |
| 5,851,832 A | 12/1998 | Weiss et al. | 435/368 |
| 5,958,767 A | * 9/1999 | Snyder et al. | 435/368 |

OTHER PUBLICATIONS

Snyder, E., et al., *Nature (London)* 374:367–370, 1995.
Weiss, S., et al., *Trends Neurosci*.19:387–393, 1996.
McKay, R., *Science* 276:66–71, 1997.
Snyder, E., et al., *Proc. Natl. Acad. Sci. USA* 94:11663–11668, 1997.
Flax, J.D., et al., *Nat. Biotech.* 16: 1033–1039, 1998.
Topf, N., et al., *Gene Ther.* 5:507–513, 1998.
Svendsen, C.N., Alzheimer's Research 3:131–135 (1997).
Barba, D., et al., J. Neurosurg. 79:729–735 (1993).
Takamiya, et al., J. Neurosurg. 79:104–110 (1993).

\* cited by examiner

*Primary Examiner*—James Ketter
(74) *Attorney, Agent, or Firm*—Nixon Peabody LLP

(57) ABSTRACT

Stable clones of neural stem cells (NSCs) have been isolated from the human fetal telencephalon. In vitro, these self-renewing clones (affirmed by retroviral insertion site) can spontaneously give rise to all 3 fundamental neural cell types (neurons, oligodendrocytes, astrocytes). Following transplantation into germinal zones of the developing newborn mouse brain, they, like their rodent counterparts, can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny. Readily genetically engineered prior to transplantation, human NSCs are capable of expressing foreign transgenes in vivo in these disseminated locations. Further supporting their potential for gene therapeutic applications, the secretory products from these NSCs can cross-correct a prototypical genetic metabolic defect in abnormal neurons and glia in vitro as effectively as do murine NSCs. Finally, human cells appear capable of replacing specific deficient neuronal populations in a mouse model of neurodegeneration and impaired development, much as murine NSCs could. Human NSCs may be propagated by a variety of means—both epigenetic (e.g., chronic mitogen exposure) and genetic (transduction of the propagating gene vmyc)—that are comparably safe (vmyc is constitutively downregulated by normal developmental mechanisms and environmental cues) and effective in yielding engraftable, migratory clones, suggesting that investigators may choose the propagation technique that best serves the demands of a particular research or clinical problem All clones can be cryopreserved and transplanted into multiple hosts in multiple settings.

4 Claims, 6 Drawing Sheets

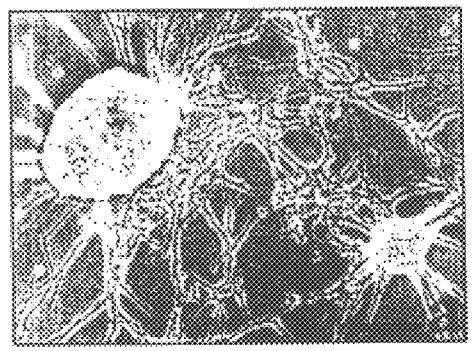
FIG. 2A
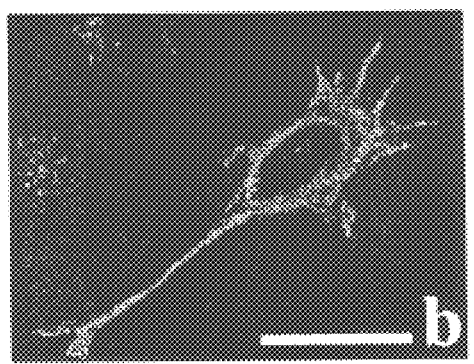
FIG. 2B
   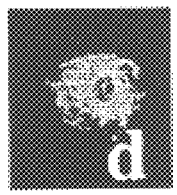   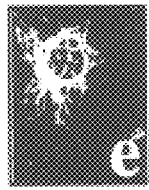
FIG. 2C      FIG. 2D      FIG. 2E

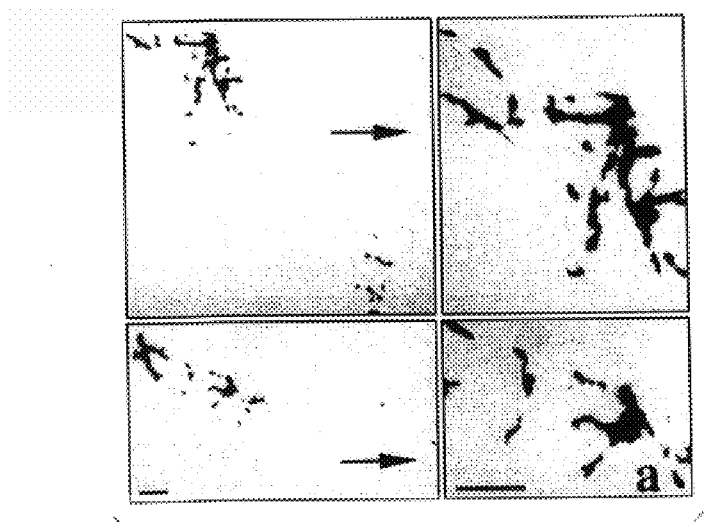
*FIG. 5A*
*FIG. 5D*
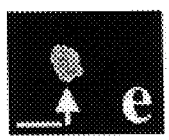
*FIG. 5E*
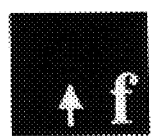
*FIG. 5F*
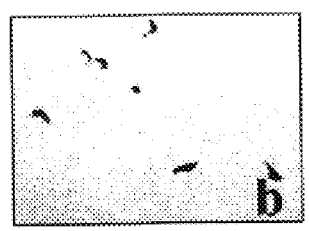
*FIG. 5B*
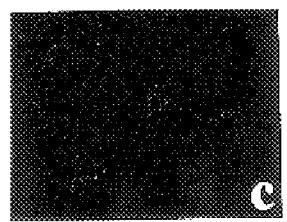
*FIG. 5C*
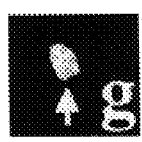
*FIG. 5G*
 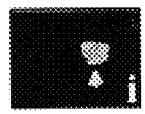 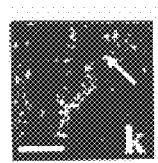 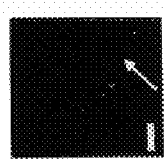
*FIG. 5H*   *FIG. 5I*   *FIG. 5K*   *FIG. 5L*
 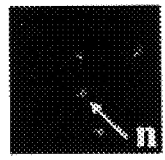
*FIG. 5M*   *FIG. 5N*
*FIG. 5J*
  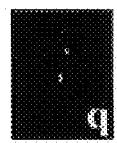
*FIG. 5O*   *FIG. 5P*   *FIG. 5Q*

ENGRAFTABLE HUMAN NEURAL STEM CELLS

This is a continuation of application Ser. No. 09/133,873, filed on Aug. 14, 1998 now U.S. Pat. No. 5,958,767.

INTRODUCTION

Neural stem cells (NSCs) are postulated to be relatively primordial, uncommitted cells that exist in the developing and even adult nervous system and are responsible for giving rise to the array of more specialized cells of the mature CNS[1-12]. They are operationally defined by their ability (a) to differentiate into cells of all neural lineages (neurons—ideally of multiple subtypes, oligodendroglia, astroglia) in multiple regional and developmental contexts (i.e., be multipotent); (b) to self-renew (i.e., also give rise to new NSCs with similar potential); (c) to populate developing and/or degenerating CNS regions. An unambiguous demonstration of monoclonal derivation is obligatory to the definition—i.e., a single cell must possess these attributes. With the earliest recognition that rodent neural cells with stem cell properties, propagated in culture, could be reimplanted into mammalian brain where they could reintegrate appropriately and stably express foreign genes[13-16], gene therapists and restorative neurobiologists began to speculate how such a phenomenon might be harnessed for therapeutic advantage as well as for understanding developmental mechanisms. These, and the studies which they spawned (reviewed elsewhere[2-9-11,17-21]) provided hope that the use of NSCs—by virtue of their inherent biology—might circumvent some of the limitations of presently available graft material and gene transfer vehicles and make feasible a variety of novel therapeutic strategies[20-22].

Neural cells with stem cell properties have been isolated from the embryonic, neonatal and adult rodent CNS and propagated in vitro by a variety of equally effective and safe means—both epigenetic (e.g., with mitogens such as epidermal growth factor [EGF] or basic fibroblast growth factor [bFGF][1,5,16,23-27] or with membrane substrates[7]) and genetic (e.g., with propagating genes such as vmyc or SV40 large T-antigenis[1,9-15,17-19,28-32]). Maintaining such NSCs in a proliferative state in culture does not appear to subvert their ability to respond to normal developmental cues in vivo following transplantation—to withdraw from the cell cycle, interact with host cells, differentiate appropriately[9-16,29-33]. These extremely plastic cells migrate and differentiate in a temporally and regionally appropriate manner particularly following implantation into germinal zones throughout the brain. They participate in normal development along the murine neuraxis, interiningling non-disruptively with endogenous progenitors, responding similarly to local microenvironmental cues for their phenotypic determination and appropriately differentiating into diverse neuronal and glial cell types. In addition, they can express foreign genes (both reporter genes and therapeutic genes) in vivo[9-21,29-32], and are capable of specific neural cell replacement in the setting of absence or degeneration of neurons and/or glia[9,11,31,32].

SUMMARY OF THE INVENTION

This paper affirms the potential of clones of human NSCs to perform these critical functions in vitro and in vivo. We show them to be multipotent, self-renewing, engraftable, plastic, and migratory; to secrete gene products that can cross-correct a prototypical neurodegenerative genetic enzymatic defect (a necessary precursor for gene therapy of such diseases); to pursue in vivo (following transplantation into various germinal zones) developmental programs appropriate to a given region and stage (even if different from that from which the cells were initially obtained); to be capable of ex vivo genetic manipulation—e.g., retroviral-mediated transduction of a foreign gene—and to be capable, following transplantation, of expressing that transgene in vivo in widely disseminated CNS regions (further establishing gene delivery/therapy potential); and to be capable of differentiating towards replacement of specific deficient neuronal populations in a prototypic mouse mutant model of neurodegeneration and impaired development (suggesting a potential for therapeutic CNS cell replacement). Comparison is also made between the capabilities of human NSCs propagated by either epigenetic (with bFGF) or genetic (via a constitutively downregulated vmyc ) means; the findings suggest that these two common means of propagation are equally effective and safe (inferring that investigators may freely choose the technique that best fits their research or clinical demands.)

DETAILED DESCRIPTION OF THE INVENTION

We present evidence that neural cells with rigorously defined stem cell features, may, indeed, be isolated from the human brain and may emulate the behavior of NSCs in lower mammals. Not only do these observations vouchsafe conservation of certain neurodevelopmental principles to the human CNS, but they suggest that this class of neural cells may ultimately be applied as well to research and clinical problems in the human. Indeed, not only might the actual human NSC clones described in this report serve that function, but our data suggest that other investigators may readily obtain and propagate such cells from other sources of human material through a variety of equally safe and effective methods (both epigenetic and genetic) with the expectation that such cells will fulfill the demands of multiple research and/or therapeutic problems.

The growing interest in the potential of NSCs has been analogous to that in hematopoietic stem cells. This interest derives from the realization that NSCs are not simply a substitute for fetal tissue in transplantation paradigms or simply another vehicle for gene delivery. Their basic biology, at least as revealed through the examination of cells, appears to endow them with a potential that other vehicles for gene therapy and repair may not possess. For example, that they may integrate into neural structures after transplantation may allow for the regulated release of various gene products as well for literal cell replacement. (While presently available gene transfer vectors usually depend on relaying new genetic information through established neural circuits, which may, in fact, have degenerated and require replacement, NSCs may participate in the reconstitution of these pathways.) The replacement of enzymes and of cells may not only be targeted to specific, anatomically circumscribed regions of CNS, but also, if desired, to larger areas of the CNS in a widespread manner by simple implantation into germinal zones. This ability is important because many neurologic diseases are not localized to specific sites as is Parkinson's disease. Rather their neuropathology is often extensive, multifocal, or even global (e.g., the lesions present in various traumatic, immunologic, infectious, ischemic, genetic, metabolic, or neurodegenerative processes). These are therapeutic challenges conventionally regarded as beyond the purview of neural transplantation. NSCs, therefore, have helped to broaden the paradigmatic scope of transplantation and gene therapy in the CNS. NSCs pass readily and unimpeded through the blood-brain barrier and deliver their foreign gene products immediately, directly, and, if necessary, in a disseminated fashion to the CNS. In addition, NSCs may be responsive to neurodegeneration, shifting their differentiation to compensate for deficient cell types. The biology underlying these properties may not only be of practical value but might illuminate fundamental developmental mechanisms.

To summarize our results, clones of human NSCs—unambiguously affirmed by the presence of a common retroviral insertion site and propagated by either epigenetic or genetic means—can participate in normal CNS development in vivo and respond to normal microenvironmental cues, including migration from various germinal zones along well-established migratory routes to widely disseminated regions. A single NSC is capable of giving rise to progeny in all 3 fundamental neural lineages—neurons (of various types), oligodendroglia, and astroglia (hence, multipotency)—as well as giving rise to new NSCs with similar potential (i.e., self-renewal). In vivo, following transplantation into mouse hosts, a given human NSC clone is sufficiently plastic to differentiate into neural cells of region- and developmental stage-appropriate lineages along the length of the neural axis: into neurons where neurogenesis normally persists, and into glia where gliogenesis predominates, emulating patterns well-established for endogenous murine progenitors, with which they intermingle seamlessly. Thus, for example, they will give rise to neurons following migration into the OB at one end of the neuraxis and into granule neurons in the cerebellum at the other, yet also yield astroglia and oligodendroglia, the appropriate cell types born in the postnatal neocortex, subcortical white matter, and striatum. Of additional significance, as might be expected of a true stem cell, we could demonstrate that many of the neuronal types into which these NSCs could differentiate, are born not at the developmental stage from which the cells were initially obtained (e.g. midgestation), but rather at the stage and region of NSC implantation, thus affirming appropriate temporal (in addition to regional) developmental responsiveness.

Interestingly, the most robust differentiation was ultimately not achieved in the culture dish where cells could maintain a more undifferentiated appearance for prolonged periods, but in the transplanted brain, where they rapidly pursued differentiated phenotypes. This conclusion is also supported by the observation that, for the in vitro experiments, triggering astrogliogenesis (the last cell type typically born in the developing brain) required the presence of co-cultured primary CNS cells (presumably recreating the "milieu") whereas simple implantation of the NSCs into the in vivo environment was sufficient in the transplant experiments.

Such abundant, genetically-homogeneous, manipulatable cells clearly represent a valuable model for studying human NSC biology in vivo and in vitro. In this paper, we have demonstrated that human NSC clones possess the capabilities that might lead one to expect them to be effective in true clinician situations.

We demonstrate the ability of these cells, in their widely disseminated locations (from even a single, simple implantation procedure) to express a retrovirally-transduced foreign gene (lacZ), providing promise for future therapeutic gene transfer strategies. That gene products delivered by these human NSCs might be expected to cross-correct dysfunctional neural cells of all types was suggested by our experiments demonstrating the successful delivery of an index therapeutic protein (hexosaminidase) to a prototypical model of neural cells deficient (via targeted mutagenesis) in that specific gene product (Tay-Sachs mouse cells). Tay-Sachs brain cells of neuronal, glial, and even immature neuroepithelial progenitor phenotypes could be effectively rescued by the secretory products of these human NSCs and complement them effectively. Once internalized in the target neural cells, this gene product forestalled pathologic $GM_2$ accumulation in the majority of mutated cells. This successful molecular cross-correction taken together with the cellular transplantation and in vivo migration data help establish the feasibility of human NSC-mediated strategies for the treatment of extensive inherited metabolic and other neurogenetic human diseases for which Tay-Sachs is an exemplar.

In summary, NSCs may be propagated by a variety of means (both epigenetic and genetic) that are comparably effective and safe in yielding engraftable, responsive neural cells (and may, in fact, access common final molecular pathways that interact reversibly with cell cycle regulatory proteins ). Therefore, insights gained from studies of NSCs perpetuated by one technique may be legitimately joined with insights derived from studies employing others to help provide a more complete picture of NSC biology. Furthermore, in helping to resolve debate in the NSC literature as to which techniques are most effective for isolating and manipulating NSCs, and doing so with cells of human origin, the door is open for investigators and/or clinicians to pick the propagation technique that best serves the demands of their particular research or clinical problem. These may have significant practical implications. It is interesting. that propagating NSCs by genetic means (e.g. a vmyc construct that is constitutively downregulated by normal developmental mechanisms and environmental cues) appears to be among the safest, easiest, most efficacious, reliable, and cost-effective methods to date for many needs.

BRIEF DESCRIPTION OF THE DRAWINGS

FIGS. 2A–2E: Characterization of human neural stem cells (NSCs)in vitro. [A] NSCs tend to grow as clusters in serum-free bFGF-supplemented medium. They differentiate spontaneously into neurofilament-immunoreactive neurons [B] or CNPase-immunoreactive oligodendrocytes [C] when transferred to serum-containing medium, or into GFAP-expressing astrocytes when co-cultured with primary murine CNS cultures (and identified with a human-specific anti-GFAP antibody) as, for example in [D], illustrating a typical type-1 protoplasmic astrocyte. Hence, a single clone has the potential for generating cells of all neural lineages ("multipotency"). New immature, undifferentiated, vimentin-immunoreactive NSCs [E] are present in clones under all conditions, suggesting the ability of a clone to "self-renew" (i.e., produce new multipotent NSCs).

FIGS. 5A–5Q: Differentiation and disseminated foreign gene (β-galactosidase) expression of human neural stem cell (NSC) clones in vivo following engraftment into the SVZ of developing, neonatal mice. [A-C] Stably engrafted, β-galactosidase (βgal)-expressing, donor-derived cells from representative human NSC clone H1, detected with Xgal histochemistry [A,B] and with anti-βgal ICC [C]. The donor-derived cells pictured in the series of photomicrographs in [A] are within the periventricular and subcortical white matter regions (as per FIG. 4). (The top and bottom panels—low power on the left, corresponding high power on the right—are from representative semi-adjacent regions within a single recipient, suggesting a significant distribution of cells; arrows indicate the lateral ventricles). Furthermore, as illustrated in [B,C] by representative high power photomicrographs through the olfactory bulb (OB) (located as in FIG. 4D), donor-derived cells from this clone have not only migrated extensively to this developmentally-appropriate site, but continue to express βgal in this distant location (i.e., in a disseminated fashion in vivo). The normal fate of a subpopulation of SVZ-derived progenitors that have migrated to the OB at this developmental stage is to become neuronal In [D–G], donor-derived neurons in the mature OB, derived from BrdU-labeled NSCs (representative clone H6 implanted into the SVZ at birth, are identified by both their immunoreactivity to a human-specific NF antibody [D] as well as their expression of the mature neuronal marker, NeuN [E–G]; under confocal microscopy, a BrdU+ (hence, donor-derived) cell (arrow in [E], fluorescein) is NeuN+ (arrow in [F], Texas Red) appreciated best with a dual filter (arrow in [G]). Adjacent to this representative donor-derived BrdU+/NeuN+ neuron (arrow), are 2 host OB neurons (BrdU−/NeuN+ in [G]) which share a similar size, morphology, and location with the donor-derived cell [arrow in F]. [H,I] High power view of a representative donor-derived (clone H6) oligodendrocyte (arrow), appropriately in the adult subcortical white matter (as per FIG. 4C) following neonatal intraventricular implantation, double-labeled with an antibody to the oligodendrocyte-specific protein CNPase [H] and BrdU [I]. Characteristic cytoplasmic processes extending from the soma are noted (arrowhead in [H]). The morphology of the CNPase+cell has been somewhat damaged by the HCl pre-treatment required for BrdU double-labeling). [J] Mature donor-derived astrocytes (clone H6) in the adult subcortical white matter (arrow) (as per FIG. 4C) and striatum following neonatal intraventricular implantation, identified with a human-specific anti-GFAP antibody. The inset better illustrates at higher magnification the characteristic mature astrocytic morphology of a representative human-GFAP+cell. [K–Q] Expression of vmyc is down-regulated within 48 hours following engraftment. [K], [M], and [O] are DAPI-based nuclear stains of the adjacent panels [L], [N], and [P, Q], respectively. Representative human NSC clone H6 was generated (as was the well-characterized murine NSC clone C17.2) with the propagating gene vmyc. vmyc immunoreactivity in H6-derived cells (red) in the SVZ (arrows) at 24 hours following engraftment ([L] and at higher power in [N]), is persistently absent [P] in integrated H6-derived cells (visualized by BrdU labeling in [Q] (shown here 3 weeks following transplantation, but representative of any point 24 hours after engraftment). Scale Bars: [A], [K] and applies to [L]: 100 µm; [D], [E] and applies to [F,G], [H] and applies to [I], [J], [M] and applies to [N]: 10 µm; [)] and applies to [P,Q]: 50 µm

EXPERIMENTAL PROTOCOL

Figure 1A:
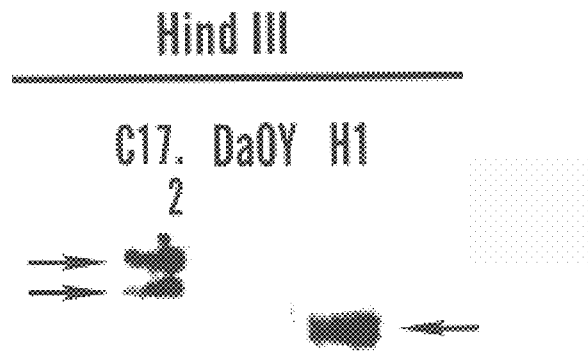
FIGS. 1A and 1B: The monoclonal nature of each putative human neural stem cell (NSC) clone is confirmed by demonstrating a single retroviral insertion site within the genomes of each. [A] Genomic DNA from the putative human NSC clone H1 (which was propagated in bFGF and subsequently transduced with a retrovirus encoding lacZ and neo) was digested with Hind III (which cuts only once within the provirus) and incubated with a radiolabeled nucleotide probe complementary to neo. Monoclonal derivation is confirmed by the presence of a single integrated retrovirus with an integration site common to all cells in the colony indicating that they were derived from a single infected "parent" cell (arrow). As a positive control, the murine NSC clone C17.2 which contains 2 integrated retroviruses encoding neo (one from an integrated vmyc-encoding retrovirus and one from a separate lacZ-encoding retrovirus[13,28] appropriately shows 2 bands (arrows). Specificity of the probe is demonstrated by the negative control, the human meduloblastoma cell line DaOY, which, having not been infected with a retrovirus, shows no neo sequences in its genome and hence no hybridization product. [B] Genomic DNA from putative clones H9, H6, D10, and C2 (human NSC colonies propagated in bFGF and/or EGF and then subsequently infected with a retrovirus encoding the propagating gene vmyc) were digested with Bgl II or Bam HI (each of which cuts only once within the provirus) and then subjected to Southern analysis utilizing a probe complementary to the proviral vmyc. Single retroviral integration sites are appreciated in all colonies confirming the monoclonal nature of each putative clone. The murine NSC clone C17.2, which contains a single copy of vmyc[13,28] and serves as a positive control, also has one band. As in [A], the negative control non-virally infected human DaOY cells, have no bands.

Maintenance and Propagation of Human NSCs in Culture. A suspension of primary dissociated neural cells ($5\times10^5$ cells/ml), prepared from the telencephelon (particularly the periventricular region) of a 15 week gestational human fetus (detailed elsewhere[55]) was plated on uncoated tissue culture dishes (Corning) in the following growth medium: Dulbecco's Modified Eagles Medium (DMEM) plus F12 medium (1:1) supplemented with N2 medium (Gibco) to which was added bFGF (10–20 µg/ml) (Calbiochem)+heparin (8 µg/ml) and/or EGF (10–20 µg/ml). Medium was changed every 5 days. Cell aggregates were dissociated when >10 cell diameters in size as follows: rinsed twice with Hank's balanced salt solution and Hepes buffer, placed in trypsin-EDTA (0.05%) for 15 min. at 37° C., triturated in soybean trypsin inhibitor, pelleted by gentle centrifugation, and replated in growth medium as above at $5\times10^5$ cells/ml.

Differentiating Culture Conditions. Dissociated NSCs were plated on poly-1-lysine (PLL)-coated, 8-well chamber slides (Nunc) in DMEM+10% fetal bovine serum (FBS) (Gibco) and processed weekly (up to 4 wks in vitro) for ICC. In most cases, differentiation occurred spontaneously. For astrocytic maturation (as assessed by immunoreactivity to a human-specific anti-GFAP antibody), human clones were co-cultured with primary dissociated cultures of newborn CD-1 mouse brain.

Retrovirus-Mediated Gene Transfer into Human NSCs. Two different xenotropic, replication-incompetent retroviral vectors were used to infect human NSCs. A retroviral vector encoding lacZ transcribed from the viral long terminal repeat (LTR) plus neo transcribed from an internal SV40 early promoter was similar to the BAG vector[13] except that it bore a PG13 xenotropic envelope. This vector not only provided a stable, histochemically- and immuno-detectable genetic marker for transplantation experiments but also enabled confirmation of monoclonality through the demonstration of a single, common retroviral insertion site on Southern analysis of cells present in a given colony. An amphotropic replication-incompetent retroviral vector encoding vmyc (transcribed from the LTR plus neo transcribed from an internal SV40 early promoter) not only permitted the propagation of human NSC clones by genetic means, but also enabled confirmation of the monoclonal origin of all progeny, as described above. This amphotrophic vector was generated using the ecotropic retroviral vector encoding vmyc (as described for generating the murine NSC clone C17.2[13,28]) to infect the GP+envAM12 amphotropic packaging line[54]. Successful infectants were selected and expanded. Supernatants from these new producer cells contained replication-incompetent retroviral particles bearing an amphotrophic envelope at a titer of $4\times10^5$ CFUs which efficiently infected the human neural cells as indicated by G418-resistance. No helper or replication-competent recombinant viral particles were produced. Infection of bFGF and/or EGF-maintained human neural cells with either vector followed similar procedures: 3 ml of supernatant ($4\times10^5$ CFUs) from the respective packaging line were added to suspensions of target cells in 2 ml growth medium+ polybrene (8 $\mu$g/ml) and incubated for 4 hrs at 37° C.; the medium was then replaced with fresh growth medium; infection was repeated 24 hrs later; 72 hrs following the second infection, infected cells were selected with G418 (0.3–1.0 mg/ml) for 10 days and individual clones were generated by limiting dilution and propagated as described below. Monoclonality in all cases was confirmed by identifying a single genomic insertion site on Southern analysis for either the lacz- or the vmyc-encoding virus as described below.

Cloning of Human NSCs. Cells were dissociated as above, diluted to a concentration of 1 cell/15 $\mu$l in growth medium and plated at 15 $\mu$l well of a Terasaki dish. Wells with single cells were noted immediately after plating. Single cell clones were expanded and maintained in bFGF-containing growth medium. Because a retrovirus integrates once randomly into the genome of a host cell with each infection event, its insertion site serves as a unique molecular tag; all progeny of that cell will also bear that and only that tag. Monoclonality in all cases was, therefore, then confirmed by identifying in all progeny a single and identical genomic insertion site on Southern analysis for either the lacZ- or the vmyc-encoding virus. Hybridization to a radiolabeled probe complementary to unique viral sequences yields 1 band at a given molecular weight per retroviral integration site. Probes were generated to either vmyc or to the neo portion of the lacZ-encoding vector as appropriate to the clone. The vmyc probe was generated by nick translation labeling with $^{32}$p dCTP. The neo probe was generated by PCR utilizing $^{32}$p dCTP. Genomic DNA was isolated from the putative human NSC clones by standard procedures and digested with restriction endonucleases that cut only once within the integrated provirus with remaining cuts only in the flanking regions. For analysis with the vmyc probe, DNA was digested with Bgl II or Bam HI; for the neo probe, DNA was cut with Bgl II. The remainder of the Southern analysis followed standard procedures. The non-virally infected DaOY human cell line, which should have no detectable bands, served as a negative control. (To insure the health of clones once generated, particularly when small, 10% FBS and 5% horse serum (HS) were occasionally added to the medium.)

Cryopreserving Human NSC Clones. Trypsinized human cells were pelleted and resuspended in a freezing solution composed as follows: 10% DMSO (Sigma), 50% FBS, 40% bFGF-containing growth medium. Divided into 1.5 ml Nunc vials, the suspension was slowly brought to −140° C. for long-term storage. Cells were thawed by placing vials in a 37° C. water bath and, following gentle removal from the vial, resuspended and cultured in excess growth medium which was changed initially after 8 hrs. to clear the DMSO.

Cross-Correction of Mutation-Induced $\beta$-Hexosaminidase Deficiency. Human NSCs were maintained as described above. The murine NSC clones "C17.2" and "C17.2H" (the latter a subclone of C17.2 transduced with a retrovirus encoding the human $\alpha$-subunit of $\beta$-hexosaminidase[30]), were maintained in similar serum-free conditions. NSCs were co-cultured in a transwell system (as detailed under Results) with primary dissociated neural cultures[13] from the brains of neonatal mice—either wildtype or $\alpha$-subunit null (Tay-Sachs) mice[39]. These primary cultures were prepared under serum-free conditions (trypsin was inactivated with soybean trypsin inhibitor), plated onto PLL-coated 12 mm glass coverslips, and maintained in the culture medium described above for NSCs; in one set of control conditions, bFGF+heparin were excluded from the medium; the results were unaffected, however. The presence of hexosaminidase activity was assayed by standard histochemical techniques[30]: Cells were fixed in 4% paraformaldehyde (PFA), washed in 5 mM citrate buffer (pH 4.4), and incubated with NASBG (0.25 mM) in 50 mM citrate buffer (pH4.5) for 3 hrs at 40° C. Subsequently, they were exposed to the same substrate in the presence of 1:1000 diluted pararosaniline hexasonium salt for 2–3 hrs at 20° C. Hexosaminidase-containing cells stain increasingly pink-red in direct proportion to their level of enzyme activity[30]. NASBG staining of primary neural cells from dissociated brains of wildtype mice served as a positive control for both the intensity of normal staining (identical to that in FIGS. 3B,C) and the percentage of NASBG+cells (~100%). Neural cell types in the primary dissociated cultures were identified by ICC for standard neural cell type-specific markers: for neurons, NeuN (1:100); for astrocytes, GFAP (1:500); for oligodendrocytes, CNPase (1:500); for immature, undifferentiated neuroepithelial-derived progenitors, nestin (1:1000). The presence of the $\alpha$-subunit of human $\beta$-hexosaminidase was detected via ICC with a specific antibody[30]. Cells were assessed for dual immunoreactivity to that antibody and to the neural cell type-specific antibodies in order to assess which types of mutant Tay-Sachs CNS cells had internalized the cross-corrective enzyme from the human NSCs. Intracytoplasmic $GM_2$ ganglioside was also recognized a specific antibody[39].

Transplantation. NSCs, dissociated as above, were resuspended at $4\times10^4$ cells/$\mu$l in phosphate buffered saline (PBS)+0.045% trypan blue and maintained well-triturated on ice until transplanted. For some transplant paradigms, the lateral cerebral ventricles of cryoanesthetized postnatal day 0 (P0) mice were visualized by transillumination, and a 2 $\mu$l cell suspension was injected gently into each ventricle via a pulled glass micropipette as previously described[29,30]. For EGL transplants, the cerebella of P0 mice were transilluminated and a 2 $\mu$l cellular suspension was similarly implanted directly into the EGL of each cerebellar hemisphere and the vermis as previously described[13,31]. These animals were sacrificed after the completion of cerebellar organogenesis. All transplant recipients and untransplanted controls received daily cyclosporin (10 mg/kg IP) (Sandoz) beginning on the day of transplant.

Detection and Characterization of Donor Human NSCs In Vivo. Transplanted mice were sacrificed and perfused with 4% PFA (in 0.1M PIPES buffer, pH 6.9) at serial time points: P1, P2, and weekly through 5 weeks of age. Brains were cryosectioned at 20 $\mu$m intervals. Donor-derived cells were recognized in a number of ways. Cells which had been transduced with lacZ were identified by either Xgal histochemistry or by ICC with an anti-$\beta$gal antibody as detailed below[13,32]. All NSCs (even those carrying lacZ) were prelabeled prior to transplantation with BrdU or with the non-diffusible vital red fluorescent membrane dye PHK-26 (Sigma). For BrdU labeling, 20 μM of the nucleotide analog was added to cultures 48 hrs prior to transplantation; these cells were subsequently identified in vivo by an anti-BrdU antibody as described below. PHK-labeled cells, prepared as per the manufacturer's instructions, were detected by fluorescence through a Texas Red (TR) filter. The presence of human donor-derived cells in mouse hosts and the confirmation of the human origin of specific neural cell types in vivo was also confirmed through the use of human-specific anti-neural cell type antibodies and through FISH using a probe specific for the human chromosomal centromere. Both procedures are described below. To visualize cellular nuclei of both host and donor cells and to help confirm anatomical location and relationships, some sections were also incubated (for 10 min at 20° C.) in the blue fluorescent nuclear label DAPI.

ICC. ICC with human-specific anti-neural cell type antibodies was performed using standard procedures. Cryosections from engrafted brains were permeabilized in 0.3% Triton X-100 and incubated overnight at 4° C. with an anti-human-NF antibody (1:150; Boehringer) or with an anti-human-GFAP antibody (1:200; Stemberger). Immunoreactivity was revealed by a fluorescein-conjugated anti-mouse IgG secondary antibody (1:200; Vector). Sections were also incubated in DAPI to visualize cellular nuclei. When donor-derived cells were to be recognized by the presence of βgal or BrdU, then the phenotypes of these cells were characterized by incubating tissue sections with antibodies to either βgal or BrdU in conjunction with antibodies to neural cell type-specific markers. Sections for βgal immunostaining (1:1000, Capel) were prepared as above. To reveal BrdU-intercalated cells via ICC, tissue sections were prepared somewhat differently. They were rehydrated in PBS, incubated in 2N HCl at 37° C. for 30 min, washed twice in 0.1M sodium borate buffer (pH 8.3), washed thrice in PBS, permeabilized in 0.3% Triton X-100, and incubated with an anti-BrdU antibody (1:10; Boehringer) at 37° C. for 1 hr. Immunoreactivity was revealed with either a fluorescein-conjugated (1:250; Jackson) or a biotinylated (1:200; Vector) secondary antibody. The neural cell type-specific antibodies employed were as follows: anti-NF (1:250; Stemberger) and anti-NeuN (1:20; gift of R. Mullen) to identify neurons; anti-CNPase (1:200–1:500; Stemberger) to identify oligodendrocytes; anti-GFAP (1:150; Sigma) to identify astrocytes. Immunostaining for these markers was revealed with a TR-conjugated secondary antibody [1:200; Vector]. Vmyc expression (unique to donor-derived cells) was assessed with an antibody to the protein (1:1000; UBI).

FISH for the Human-Specific Centromere. Animals were perfused with 4% PFA+2% gluteraldehyde. Cryosections of brain were post-fixed in 4% PFA, permeabilized in 0.2% Triton X-100, washed in PBS, incubated in 0.2N HCl for 20 mins., washed again in PBS, and then exposed to proteinase K (100 μg/ml) in 0.1M Tris, 0.005M EDTA (pH 8.0) at 37° C. for 15 mins. The sections were then washed in 0.1% glycine in PBS for 2 mins. and then in PBS for 5 mins. Sections were post-fixed again in 4% PFA, washed in PBS, and then rinsed with 50% formamide, 2×SSC for 5 mins. A digoxigenin-labeled probe, complementary to regions of the centromere present uniquely and specifically on all human chromosomes (Oncor), was then added to the sections which were coverslipped, sealed with rubber cement, denatured at 100° C. for 10 mins., and placed on ice for 5 mins. Sections were hybridized for 15 hrs at 37° C., following which they were washed in 65% formamide, then 2×SSC for 30 mins. at 430C, and then 2×SSC for 30 mins. at 37° C., and finally PBS for 15 mins. at 20° C. The probe was detected by an anti-digoxigenin TR-conjugated antibody (Boehringer) diluted 1:5 in 0.5% BSA+5% NHS in PBS (30 mins. at 37° C.). Slides were rinsed 3 times in PBS (15 mins./wash), incubated with DAPI, rinsed again in PBS, and mounted for fluorescence microscopy.

RESULTS

Isolation, Propagation, and Cloning of Human Neural Stem Cells

The isolation, propagation, characterization, cloning, and transplantation of NSCs from the human CNS followed a "blueprint" propagated following trasduction of a constitutively downregulated vmyc and growth factor-(especially bFGF-) expanded NSC clones, Based on the observation that NSCs—even genetically propagated clones[34]—appear to divide in response to bFGF and EGF in serum-free medium[5,35], this dual responsiveness was chosen as a method for both screening and for enriching a starting population of dissociated primary human neural tissue for cells that fulfilled this requirement. In addition, the primary neural cells were initially obtained (to the best of our ability) from a region of the CNS postulated to harbor (in lower mammals) a relatively rich population of NSCs, the ventricular zone (VZ) of the fetal telencephelon[1,7,8,23].

Dissociated neural cells from a 15 week human fetal brain were initially grown as a polyclonal population in serum-free medium containing bFGF and/or EGF. The cultured cells were often transferred between media containing one or the other of the two mitogens in order to establish and select for dual responsiveness. Some populations were then maintained in bFGF alone for subsequent manipulation and cloning as described below; others were used for retrovirally-mediated transduction of vmyc and subsequent cloning, also as described below.

In order to provide an unambiguous molecular tag for assessing the clonal relationships of the cells, as well as to facilitate identification of some cells following transplantation and to assess their capacity to express exogenous genes in vivo, some bFGF-propagated subpopulations were infected with an amphotropic replication-incompetent retroviral vector encoding both lacZ (the gene for E. coli β-galactosidase [βgal]) and neo (the gene for neomycin resistance). Infected cells were selected for survival in G418 (a neomycin analog). Single colonies were initially isolated by limiting dilution; monoclonality of the cells in a given colony was then confirmed by demonstrating that only one copy of the lacZ/neo-encoding retrovirus, with a unique chromosomal insertion site, was present. Genomic DNA from individual colonies, digested with restriction endonucleases that cleaved once in the integrated provirus, were subjected to Southern analysis with a radiolabeled probe complementary to neo. In clone H1, for example, all lacZ/neo+ cells, indeed, had a single, common retroviral integration site indicating that they were derived from a single infected "parent" cell [FIG. 1A].

Figure 1B:
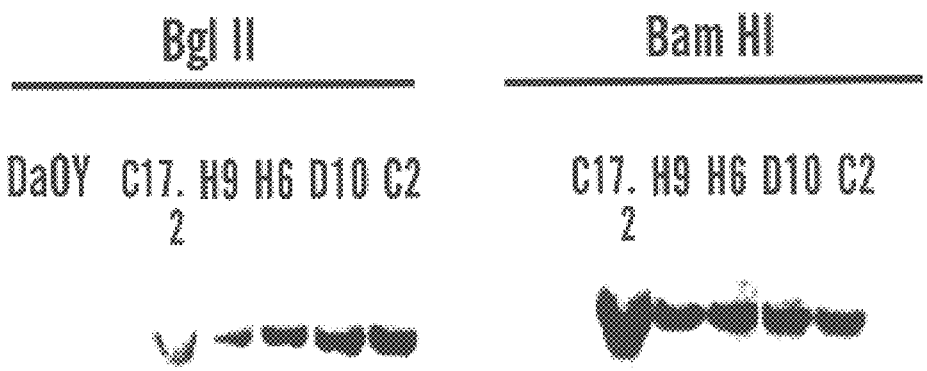

Some populations, enriched for human NSCs as described above, were transduced with vmyc, yielding multiple stable clones. Specifically, bFGF-maintained cells were infected with an amphotropic, replication-incompetent retroviral vector encoding vmyc and neo[28]. Individual, G418-resistant colonies were isolated and maintained as separate cultures. Again, monoclonality of each colony was affirmed by demonstrating that each putative clone had only one unique retroviral insertion site [FIG. 1B]. All vmyc-transduced human cell colonies (as well as the established murine NSC clone C17.2, included as a positive control) produced single bands of the same molecular weight following endonuclease bisection of the provirus and hybridization to a vmyc probe. Thus, as was the case for the epigenetically-maintained cells, all the vmyc transduced colonies were monoclonal. Five clones (H6, H9, D10, C2, E11) were generated by this procedure and were maintained in serum-free medium containing bFGF.

To be classified as a NSC, a given cell must yield progeny in all neural lineages and give rise to other single cells that can do so; therefore, it was imperative to affirm unambiguously that all cells in a given colony were members of the same clone. Having met this obligate criterion, additional characterization of clones could proceed.

In Vitro Characterization of Clones
Multipotency and Self-Renewal

In uncoated dishes and in serum-free medium supplemented with bFGF, all clones grew in culture as clusters that could be passaged weekly for at least 1 year [FIG. 2A]. The cells within these clusters expressed the intermediate filament vimentin, a frequently used and reliable marker for immature multipotent neural progenitors[25]. By dissociating these clusters and plating them in serum-containing medium, these clones differentiated spontaneously into neurons and oligodendrocytes [FIGS. 2B,D], a technique previously used for differentiating bFGF-propagated rodent NSCs and progenitors[16,25,37]. After 5 days under these differentiating conditions, a majority of the cells (90%) in all clones became immunoreactive for the neuronal marker neurofilament (NF) [FIG. 2B], while a smaller proportion (10%) expressed CNPase, a marker for oligodendroglia [FIG. 2C]. Mature astrocytes expressing glial fibrillary acidic protein (GFAP) were not initially appreciated under these culture conditions, even after one month in vitro. However, GFAP expression could be induced in these human clones by co-culture with primary dissociated embryonic murine CNS tissue [FIG. 2D]. In addition to cells expressing the variety of differentiated lineage-specific markers noted above (establishing "multipotency"), each clone also gave rise to new immature vimentin+cells [FIG. 2E] which could, in turn, on subsequent passages, give rise to new cells expressing multiple differentiated neural markers as well as to new vimentin+passageable cells (i.e., "self-renewability").

These results affirmed that all of the clones to be studied in vitro and in vivo following transplantation fulfilled the operational definition of NSCs: stable, self-renewing, multipotent vimentin+clones derived from a single cell with the capacity for differentiating into progeny in all 3 fundamental neural lineages. All the clones, whether genetically-modified or epigenetically-maintained, were remarkably similar in their behaviors and phenotypes in vitro. To continue this comparison, these various clones were used in parallel in the in vivo transplant experiments described below.

Storage

Of note, all clones could be efficiently cryopreserved (detailed under Experimental Protocols) with minimal adverse effects on cell viability and no discernible effect on proliferation or differentiation upon thawing.

Ability to Complement and Cross-Correct a Genetic Defect

To help assess their potential as vehicles for molecular therapies, we next evaluated, under well-controlled and observable conditions, the ability of human NSCs to complement and cross-correct a prototypical genetic, metabolic defect with the same efficiency as murine NSCs[30,29,38]. The index genetic defect chosen was the absence of the α-subunit of β-hexosaminidase, the mutation responsible in humans for the untreatable and inexorably neurodegenerative lysosomal storage disease, Tay-Sachs. Absence of the α-subunit leads to a deficiency in hexosaminidase A which is required to metabolize $GM_2$ ganglioside to $GM_3$. Pathologic $GM_2$ accumulation in the brain leads to the progressive neurodegeneration characteristic of the disease. The ability of human NSCs to effect cross-correction was compared with the following two well-established murine NSCs: "clone C17.2" and a subclone of C17.2 (called "clone C17.2H") engineered via retroviral transduction of the α-subunit to overexpresses hexosaminidase[30]. Previous studies using these murine NSC clones established that they both synthesized and secreted significant amounts of functional hexosaminidase A which could be endocytosed by fibroblasts from human Tay-Sachs patients[30]. The recent generation of a transgenic mouse in which the gene encoding the α-subunit was specifically mutated[39] now permitted an examination of the capacity of human NSCs (as well as the murine NSCs) to cross-correct actual neural cells derived from an animal model of Tay-Sachs. Furthermore, the availability of established, standardized tools for the rapid and reliable detection of the specific gene product, the lysosomal enzyme activity, and the intracellular pathologic phenotype made this model ideal.

To assess their ability to produce a secretable gene product capable of rescuing a mutant neural phenotype, NSCs (murine and human) and control cells were cultured on one side of a membrane with a pore size (0.4 μm) sufficient to allow passage of hexosaminidase but not of the cells. The membrane was partially immersed in a well on the bottom of which rested a coverslip onto which neural cells dissociated from the brain of a neonatal Tay-Sachs mouse had been plated. After 10 days of co-culture in this transwell system, the coverslips bearing the mutant neural cells were examined as follows: (1) for the presence of hexosaminidase activity, as assayed by the production of a red precipitate following exposure to napthol-AS-BI-N-acetyl-β-D-glucuroniside (NASBG) [FIGS. 3A–C,M]; (2) with both an antibody to the α-subunit and antibodies to CNS cell type-specific markers to determine which Tay-Sachs neural cell types had internalized the corrective gene product [FIGS. 3D–L]; and (3) for reduction in $GM_2$ storage [FIG. 3N].

Figure 3A:
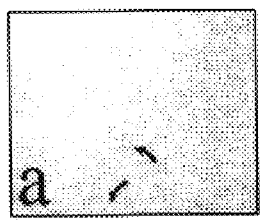
FIGS. 3A–3N: Human neural stem cells (NSCs) are capable of complementing a prototypical gene product deficiency (e.g., β-hexosaminidase-A) in neural cells of multiple lineages in which the gene is mutated (e.g., brain cells from Tay-Sachs mice). As a proof of principle that human NSCs (like murine NSCs) are capable of cross-correcting a neurogenetic defect, neural cells from the brains of mice with the prototypical neurogenetic disorder Tay-Sachs disease, generated via targeted mutagenesis of the α-subunit of β-hexosaminidase resulting in absence of hexosaminidase-A$^{39}$, were exposed to secreted gene products from human NSCs to assess their ability to effect complementation of the defect. [A–C] Hexosaminidase activity as determined by NASBG histochemistry (Nomarski optics). Functional hexosaminidase produces a red-pink precipitate with an intensity proportional to the level of activity. [A] Tay-Sachs neural cells (arrows) not exposed to NSCs have no, or minimal, detectable hexosaminidase. (A small number of faintly pink NASBG+ cells are occasionally observed reflecting low residual hexosaminidase-B activity). In comparison, Tay-Sachs neural cells exposed to secretory products from murine NSCs (e.g., clone C17.2H) [B] or from human NSCs [C] now stain intensely red (wildtype intensity) suggesting that they have been cross-corrected, i.e., have internalized significant amounts of functionally active hexosaminidase from the NSC-conditioned medium. [D–L] To help determine which neural cell types from the Tay-Sachs brain were cross-corrected, primary dissociated Tay-Sachs neural cells which had been co-cultured in a transwell system with human NSCs (as in [C]) were reacted both with a fluorescein-labeled antibody to the human a-subunit of hexosaminidase [D–F] and with antibodies to neural cell type-specific antigens (visualized by a TR-tagged secondary antibody) [G–I, respectively]. Photomicroscopy through a dual filter confirmed co-localizaton of the α-subunit with the cell-type markers [J–L, respectively]. A subset of these now α-subunit-positive corrected cells [D] were neurons, as indicated by their expression of the neuronal marker NeuN [G,J]; a subset of the α-subunit+cells [E] were glial, as illustrated by their co-expression of the glial marker GFAP [H,K]; and a subset of the α-subunit+cells [F] were immature, undifferentiated CNS precursors, as indicated by the presence of the intermediate filament nestin [I,L]. (Untreated cells from a Tay-Sachs brain do not stain for the α-subunit). [M] Percentage of successfully rescued (i.e., NASBG+) primary Tay-Sachs neural cells as seen in [A–C]. The number of "untreated" Tay-Sachs α-subunit-null cells (–/–) (i.e., unexposed to NSCs) that were NASBG+(1st histogram) was quite low. (That the percentage is not 0 reflects some low residual hexosaminidase-B activity in mutant cells that is sometimes sufficient enough in some cells to produce a pale pink scoreable cell). In contrast, among Tay-Sachs neural cells "treated" with secretory products from murine NSCs (C17.2) (2nd histogram), murine NSCs engineered to over-express hexosaminidase (C17.2H) (3rd histogram), or human NSCs (4th histogram), the percentage of cross-corrected, hexosaminidase-containing cells was significantly increased (p<0.01). The NSCs did not significantly differ from each other in their ability to effect this rescue. (NASBG staining of neural cells from a wildtype mouse served as a positive control and were nearly 100% NASBG+, histogram not presented). [N] Complementation of gene product deficiency results in rescue of a pathologic phenotype in mutated neural cells, as illustrated by percentage of Tay-Sachs CNS cells with diminished $GM_2$ accumulation. Among Tay-Sachs cells not exposed to NSCs (1st histogram), the percentage of $GM_2$+cells was large reflecting their pathologically high level of storage and consistent with a lack of enzyme as per [M]. In contrast, the percentage of cross-corrected Tay-Sachs cells without detectable $GM_2$ storage following exposure to murine (2nd and 3rd histograms, as in [M]) or human NSCs (4th histogram) was significantly lower than in the mutant (p<0.01), approaching that in wildtype (+/+) mouse brain (5th histogram). Again, the NSCs did not significantly differ from each other in their ability to effect this rescue.
Figure 3B:
Figure 3C:
Figure 3D:
Figure 3E:
Figure 3F:
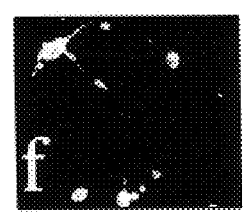
Figure 3G:
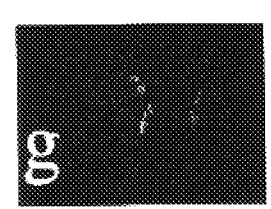
Figure 3H:
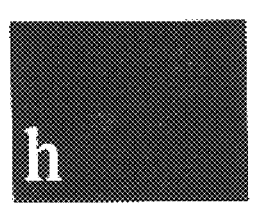
Figure 3I:
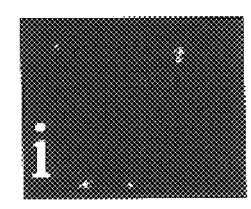
Figure 3J:
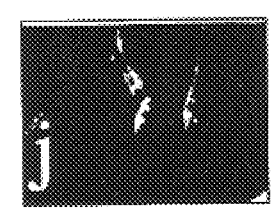
Figure 3K:
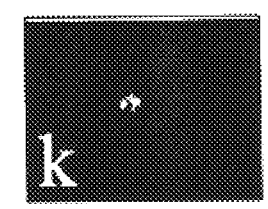
Figure 3L:
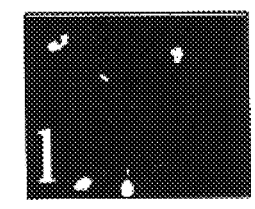
Figure 3M:
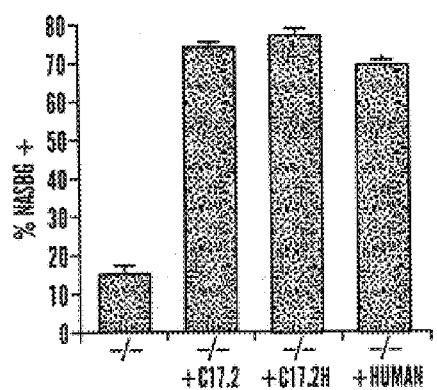
Figure 3N:
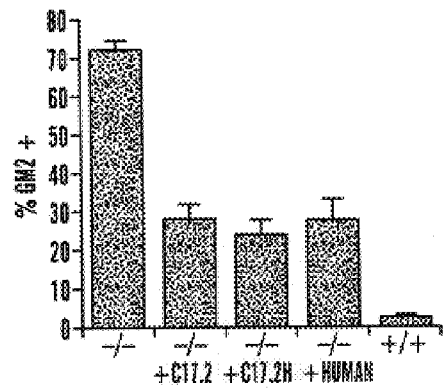
Figure 4A:
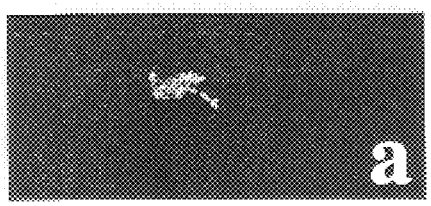
FIGS. 4A–4E: Developmentally-appropriate migration of human neural stem cells (NSCs) following engraftment into the subventricular germinal zone (SVZ) of newborn mice. [A,B] Donor-derived human NSCs integrate and intermingle nondisruptively with endogenous progenitors within the host SVZ by 24 hours after transplantation. A representative donor-derived cell with a typical short process (red), highlighted in [A], has interspersed with densely packed endogenous SVZ cells, visualized by DAPI (blue) in the overlapping image in [B]. [C] Two weeks following transplantation, many donor-derived cells (red) have migrated extensively within the subcortical white matter (arrow) and corpus callosum (c) from their site of implantation in the lateral ventricles (LV), as visualized in this coronal section. A representative migrating cell within the subcortical white matter (arrow), visualized at higher magnification in the boxed insert, is noted to have a leading process characteristic of migrating precursor cells. [D,E] As seen in this representative cresyl violet-counterstained parasagittal section, other donor-derived cells migrated from their integration site in the anterior SVZ to enter the rostral migratory stream ("RMS") leading to the olfactory bulb ("OB"). Representative BrdU-immunoperoxidase-positive (brown) donor-derived cells (arrow) within the RMS, are seen at low power in [D] and visualized at higher magnification in [E], intermixed with migrating host cells. Further characterization and visualization of these donor human NSC-derived cells in their final location in the OB are presented in FIG. 5. Scale Bars: 100 μm.
Figure 4B:
Figure 4C:
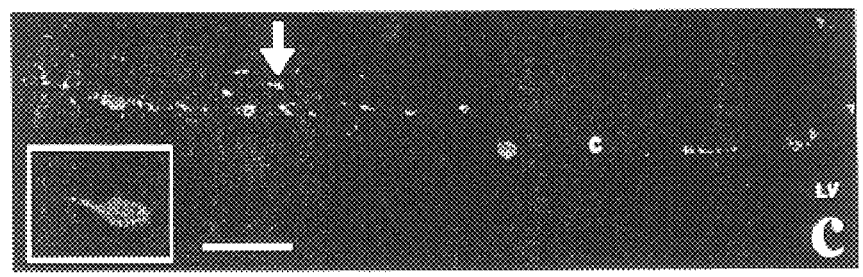
Figure 4D:
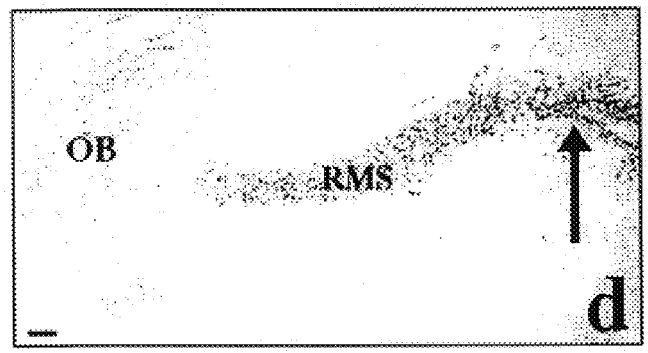
Figure 4E:
Figure 6A:
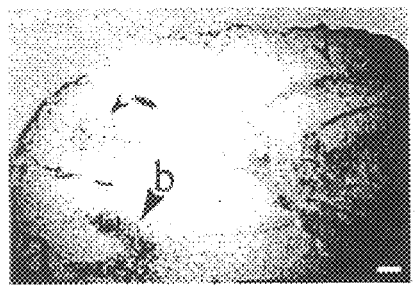
FIGS. 6A–6J: Neuronal replacement by human neural stem cells (NSCs) following transplantation into the cerebellum of the granule neuron-deficient meander tail (mea) mouse model of neurodegeneration. [A–G] BrdU-intercalated, donor-derived cells (from representative clone H6) identified in the mature cerebellum by anti-BrdU immunoperoxidase cytochemistry (brown nuclei) following implantation into the neonatal mea external germinal layer (EGL). (The EGL, on the cerebellar surface, disappears as the internal granule layer (IGL) emerges to become the deepest cerebellar cortical layer at the end of organogenesis[13]) [A] Clone H6-derived cells are present in the IGL ("igl"; arrowheads) of all lobes of the mature cerebellum in this parasagittal section. (Granule neurons are diminished throughout the cerebellum with some prominence in the anterior lobe). [B] Higher magnification of the representative posterior cerebellar lobe indicated by arrowhead "b" in [A], demonstrating the large number of donor-derived cells present within the recipient IGL. [C–G] Increasing magnifications of donor-derived cells (brown nuclei) within the IGL of a mea anterior cerebellar lobe. (Different animal from that in [A,B].) [G] Normarski optics bring out the similarity in size and morphology of the few residual host, BrdU-negative cerebellar granule neurons (arrowheads) and a BrdU+, donor-derived neuron (arrow), which is representative of those seen in all engrafted lobes of all animals.) [H,I] Confirmation of the neuronal differentiation of a subpopulation of the donor-derived, BrdU+ cells from [A–G] is illustrated by co-labeling with anti-BrdU [green in H] and the mature neuronal marker NeuN [red in I] (indicated with corresponding arrows). (Some adjacent, donor-derived cells are non-neuronal as indicated by their BrdU+ (arrowhead in [H]) but NeuN–phenotype (also illustrating the specificity of the immunostaining). [J] Cells within the IGL are confirmed to be human donor-derived cells by FISH with a human-specific probe (red) identifying human chromosomal centromeres. Scale Bars: [A], [B]: 100 µm; [F], [G], [J]: 10 µm
Figure 6B:
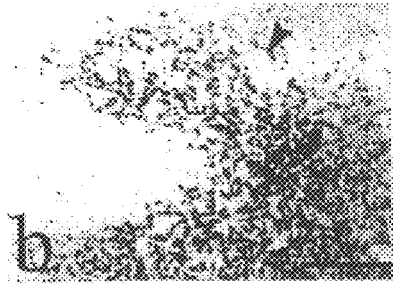
Figure 6C:
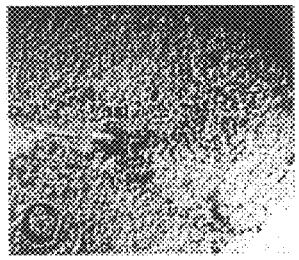
Figure 6D:
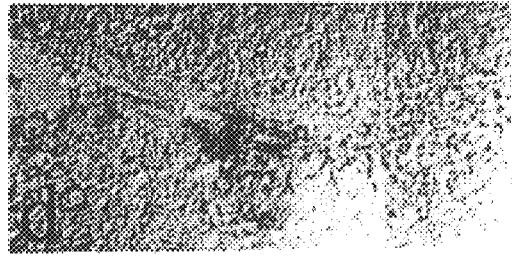
Figure 6E:
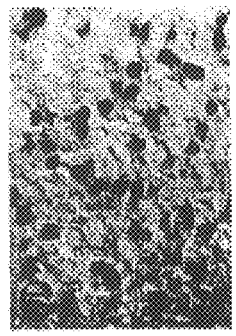
Figure 6F:
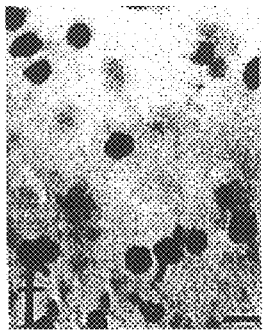
Figure 6G:
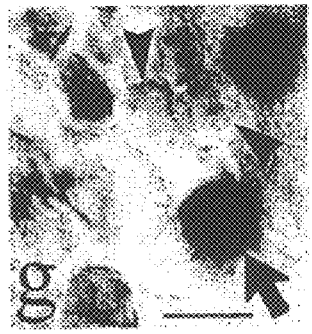
Figure 6H:
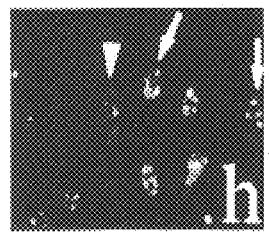
Figure 6I:
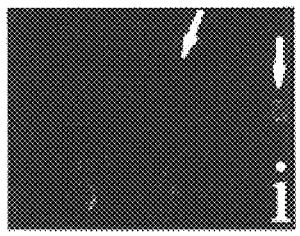
Figure 6J:
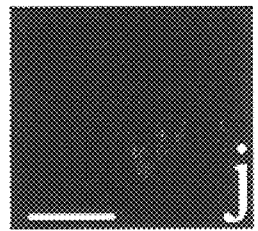

While there was minimal intrinsic hexosaminidase activity in Tay-Sachs CNS cells cultured alone [FIG. 3A], hexosaminidase activity increased to normal intensity when the cells were co-cultured with murine or human NSCs [FIGS. 3B,C]. The extent of human NSC-mediated cross-correction was as successful and efficient as that effected by murine NSCs, yielding percentages of NASBG+Tay-Sachs CNS cells significantly greater than in untreated controls (p<0.01) [FIG. 3M]. As suggested by FIGS. 3D–L, all neural cell types from the Tay-Sachs mouse brain (neurons, glia, progenitors) were corrected. As an indication that this increased enzyme activity favorably impacted the fundamental cellular neuropathologic process, the percentage of Tay-Sachs CNS cells without abnormal intracytoplasmic $GM_2$ accumulation was significantly lower in those exposed to secretory products from human NSCs than in untreated Tay-Sachs cultures (p<0.01), approaching those from wild-type mouse brain [FIG. 3N].

Therefore, human NSC clones are capable of producing and secreting a functional gene product with sufficient efficiency to be utilized by targeted impaired CNS cells of multiple lineages to correct a genetically-based defect and reduce pathology. These data help establish their validity as potential vehicles for gene therapy.

In Vivo Characterization of Clones
Multipotency, Plasticity, & Pursuit of Developmental Programs In Vivo We next determined whether human NSC clones (whether epigenetically or genetically-propagated) could not only engraft following transplantation into the immature brain, but could also respond appropriately and accommodate to normal developmental cues in vivo: migrating appropriately, integrating into host parenchyma, differentiating into neural cell types appropriate to a given region at a given developmental temporal "window"—even if that window differed from when the NSCs were obtained. Dissociated cells from the individual human NSC clones were injected bilaterally into the lateral ventricles of newborn mice, allowing them access to the SVZ. Prior to transplantation, some human cells were transduced, as detailed above, with the lacZ reporter gene. To control for and circumvent the risk of transgene downregulation (with the attendant risk of missed identification of engrafted, donor-derived cells), cells were also prelabeled either by in vitro exposure to BrdU 2 days prior to transplantation and/or with the non-diffusible vital fluorescent membrane dye PHK-26 immediately before transplantation. Stably engrafted cells were then detected, as appropriate, by Xgal histochemistry; by immunocytochemistry (ICC) with antibodies directed against BrdU, βgal, human-specific NF and/or human-specific GFAP; by fluorescence in situ hybridization (FISH) using a human-specific pan-chromosomal α-centromeric probe; and/or by PHK fluorescence. For some cells, multiple identification techniques were employed to confirm their donor, human-origin. Cell type identity of donor-derived cells was also established as necessary by dual staining with antibodies directed against neural cell type-specific markers.

Following intraventricular implantation, human NSC clones displayed developmentally-appropriate behavior, emulating that of their murine counterparts [FIGS. 4,5]. Furthermore, the engraftment, migration, and differentiation of epigenetically-perpetuated clones was identical to that of genetically-(vmyc-)perpetuated clones. (Three of the 5 clones in the latter category engrafted well [Table]; the remaining 2 clones which engrafted poorly will be discussed below). Both epigenetically- and genetically-maintained donor cells integrated into the SVZ within 48 hours following implantation [FIGS. 4A,B; 5A,K–N]. It is known that endogenous, host progenitors derived from the SVZ migrate out dorsally and laterally into the subcortical white matter and cortex over a 28 day period and become astroglia and oligodendroglia; gliogenesis predominates in those regions at that stage while neurogenesis has ceased[44]. In an analogous manner, engrafted human NSCs also migrated out extensively along the subcortical white matter by 2 weeks following engraftment [FIG. 4C], and, by 3–5 weeks, had appropriately differentiated into oligodendrocytes and astrocytes [FIGS. 5H–J]. Interestingly, the ready detection of donor-derived astrocytes in vivo [FIG. 5J] contrasts with the initial absence of mature astrocytes when human NSC clones were maintained in vitro in isolation from the in vivo environment (recall that co-culture with primary mouse CNS was required to induce astrogliogenesis [FIG. 2D]). Instructive signals emanating from other components of the murine CNS appear necessary for triggering or promoting astrocytic differentiation and/or maturation from multipotent cells.

The second known fate of endogenous SVZ progenitors is to migrate anteriorly along the RMS and differentiate into OB interneurons. By one week following transplantation, a subpopulation of donor-derived human cells from the SVZ were noted migrating along the RMS [FIGS. 4D,E]. In some cases, these cells in the RMS migrated together in small groups [FIG. 4E], a behavior typical for endogenous murine SVZ precursors[43,44]. Three weeks following transplantation, as per the expected fate of progenitors within the RMS, a subpopulation of donor-derived neurons of human origin (e.g., human-specific-NF+cells) were present within the parenchyma of the OB, intermingled with host neurons [FIGS. 5B–G, which represent high power views of sections through the OB as pictured in FIG. 4D]. Not only were these donor-derived cells human-NF+ [FIG. 5D], but, when sections through the OB were reacted with both an antibody against BrdU (to identify pre-labeled donor-derived human cells) and with an antibody to the mature neuronal marker NeuN, a large number of double-labeled BrdU+/NeuN+ donor-derived cells of human origin were integrated within the granule layer [FIGS. 5E–G], mimicking the NeuN expression pattern of endogenous, host, murine interneurons [FIGS. 5F,G]

To examine further the degree of plasticity of human NSCs, identical clones were implanted into a different germinal zone at the opposite end of the neuraxis. Transplants of the same human NSCs into the EGLs of newborn mouse cerebella appropriately yielded different neuronal cell types in this different location, primarily cerebellar granule cell interneurons in the IGL [FIGS. 6C–I], a result discussed in greater detail in the next section.

Therefore, in vivo, as in vitro [FIG. 2], all engraftable human NSC clones can give rise to cells in all 3 fundamental neural lineages—neurons [e.g., FIGS. 5D–G; 6]; oligodendrocytes [e.g., FIGS. 5H,I]; and astrocytes [e.g., FIG. 5J]. Not only did transplanted brains look histologically normal (donor cells migrated and integrated seamlessly into the host parenchyma yielding no discernible graft margins), but engrafted animals exhibited no behavioral abnormalities or other indications of neurologic dysfunction. Thus brain structures that received contributions from donor human NSCs appeared to have developed normally.

In these transplant studies, while most clones engrafted quite well, 2 of the 5 genetically-propagated NSC clones appeared to engraft poorly [Table]. Nevertheless, in vitro these clones did display characteristics seemingly identical to those of the more robustly engrafting clones. Thus, ostensibly equivalent multipotency in vitro does not necessarily translate into equivalent potential in vivo, suggesting the need for investigators to test each clone individually in transplantation paradigms. This observation further warns that transplantation of mixed polyclonal populations (the starting material for many transplantation studies presently in the literature[16,33,41,45,46]) because of their inevitable changing character and shifting representations of various clones, may be a problematic strategy.

Foreign Transgene Expression In Vivo

Gene therapy paradigms, especially for diseases characterized by extensive, multifocal, or global lesions, require that donor cells be capable of expressing foreign genes in widely disseminated locations if the clinical situation demands (in addition to being able to integrate in anatomically restricted locations[10,16,32,45,46]). The retrovirally-transduced, lacZ-expressing representative clone pictured in FIGS. 5A–C (following transplantation into the neonatal mouse cerebral ventricle and SVZ) continued to produce readily detectable βgal after migration to and stable integration and maturation within host parenchyma at distant sites in the mature animal.

Spontaneous, Constitutive, Downregulation of vmyc Expression

Interestingly and importantly, in the case of genetically-manipulated human NSC clones, the propagating gene product, vmyc, is undetectable in donor human cells beyond 24–48 hours following engraftment [FIG. 5K–Q] despite the fact that the brains of transplant recipients contain numerous stably-engrafted, healthy, well-differentiated, non-disruptive, donor-derived cells [FIGS. 4; 5A–J,Q; 6]. These observations suggest that vmyc is regulated by the normal developmental mechanisms that downregulate endogenous cellular myc in CNS precursors during mitoic arrest and/or differentiation. The loss of vmyc expression spontaneously and constitutively from stably engrafted NSCs following transplantation is consistent with the invariant absence of CNS tumors derived from implanted vmyc-propagated NSCs, even after several years in vivo[9,13,29-32]. With human NSCs, brain tumors are never seen.

Neural Cell Replacement In Vivo

Having established the probable efficacy in vitro and in vivo of human NSC-mediated foreign gene expression as a basis for gene therapy strategies, we next sought to establish whether such cells could also mediate neural cell replacement. Well-established neurologic mouse mutants have classically provided ideal models for testing specific neural cell replacement paradigms. The meander tail (mea) mutant is one such model of neurodegeneration and impaired development. Mea is characterized by a cell-autonomous failure of granule neurons to develop and/or survive in the cerebellum, especially in the anterior lobe[47]. Murine NSCs are capable of reconstituting the granule neuron-deficient IGL[31].

In order to assess their ability to replace neurons in-CNS disorders, human NSC clones were engrafted into the EGLs of newborn mea mouse cerebella When analyzed at the completion of cerebellar organogenesis, donor-derived human cells were present throughout the IGL of the cerebella [FIG. 6]. They possessed the definitive size, morphology, and location of cerebellar granule neurons [FIGS. 6E–G], identical to the few residual endogenous murine host granule neurons with which they were intermixed [FIG. 6G]. That these "replacement" neurons were of human-origin was confirmed by FISH, demonstrating the presence of cells positive for the above-described human-specific chromosomal probe [FIG. 6J]. That the human-derived cells were, indeed, neuronal was confirmed by demonstrating that most engrafted cells in the mea IGL were immunoreactive for NeuN [FIGS. 6H,J]; as in the OB, endogenous interneurons in the IGL similarly express NeuN. Thus engrafted NSCs of human origin appear sufficiently plastic to respond appropriately to varying local cues for lineage determination,

TABLE

Human Neural Stem Cell* Clones

| CLONE | PROPAGATION TECHNIQUE | ENGRAFTABLE |
| --- | --- | --- |
| H1 | bFGF | + |
| H6 | vmyc | + |
| H9 | vmyc | + |
| C2 | vmyc | + |
| D10 | vmyc | − |
| E11 | vmyc | − |

*A neural stem cell is defined as a single cell which is capable of giving rise (in vitro and/or in vivo) to neurons (of multiple types), oligodendrocytes, and astrocytes, as well as new neural stem cells. That these progeny are clonally-related to that single cell and to each other is an obligatory part of the definition. Therefore, an unambiguous demonstration of monoclonality is necessary to affirm both multipotency and self-renewal.

LITERATURE CITED

1. McKay, R. 1997. Stem cells in the central nervous system. Science 276:66–71.
2. Gage, F. H. and Christen, Y. (eds). 1997. Isolation, Charactenzation, and Utilization of CNS Stem Cells—*Research & Perspectives in Neurosciences*, Springer-Verlag, Berlin Heidelberg.
3. Morrison, S. J., Shah, N. M., and Anderson, D. J. 1997. Regulatory mechanisms in stem cell biology, *Cell* 88:287–298.
4. Stemple, D. L. and Mahanthappa, N. K. 1997. Neural stem cells are blasting off. *Neuron* 18:1–4.
5. Weiss, S., Reynolds, B. A., Vescovi, A. L., Morshead, C., Craig, C., and van der Kooy, D. 1996. Is there a neural stem cell in the mammalian forebrain. *Trends Neurosci.* 19:387–393.
6. Alvarez-Buylla, A., and Lois, C. 1995. Neuronal stem cells in the brain of adult vertebrates. *Stem Cells* (Dayt) 13:263–272.
7. Davis, A. A., and Temple, S. 1994. A self-renewing multipotential stem cell in embryonic rat cerebral cortex. *Nature* 372:263–266.
8. Williams, B. P., and Price, J. 1995. Evidence for multiple precursor cell types in the embryonic rat cerebral cortex. *Neuron* 14:1181–1188.
9. Snyder, E. Y., Neural stem-like cells: Developmental lessons with therapeutic potential, *The Neuroscientist* (in press).
10. Martinez-Serrano, A. and Bjorklund, A. 1997. Immortalized neural progenitoir cells for CNS gene transfer & repair, *Trends Neurosci.* 20:530–538.
11. Martinez-Serrano A, Snyder E Y, Neural stem cell lines for CNS repair, in *CNS Regeneration: Basic Science and Clinical Applications*, Tuszynski, M., Kordower, J., and Bankiewicz, K. (eds.) Academic Press, San Diego (in press).
12. Gage, F. H., Ray, J., and Fisher, L. J. 1995. Isolation, characterization and use of stem cells from the CNS. *Ann. Rev. Neurosci.* 18:159–92.
13. Snyder, E. Y., Deitcher, D. L., Walsh, C., Arnold-Aldea, S., Hartweig, E. A., and Cepko, C. L. 1992. Multipotent cell lines can engraft and participate in the development of mouse cerebellum. *Cell* 68:1–20.
14. Renfranz, P. J., Cunningham, M. G., and McKay, R. D. G. 1991. Region-specific differentiation of the hippocampal stem cell line HiB5 upon implantation into the developing mammalian brain. *Cell* 66:713–729.
15. Shihabuddin, L. S., Hertz, J. A., Holets, V. R. and Whittemore, S. R. 1995. The adult CNS retains the potential to direct region-specific differentiation of a transplanted neuronal precursor cell line. *J. Neurosci.* 15:6666–6678.
16. Gage, F. H., Coates, P. W., Palmer, T. D. 1995. Survival and differentiation of adult neuronal progenitor cells transplanted to the adult brain. *Proc Natl Acad Sci USA* 92:11879–11883.
17. Fisher, L. J. 1997. Neural precursor cells: application for the study & repair of the central nervous system, *Neurobiol. Dis.* 4:1–22.
18. Whittemore, S. R. and Snyder, E. Y. 1996. The physiologic relevance & functional potential of central nervous system derived cell lines, *Molecular Neurobiology* 12(1):13–38.
19. Snyder, E. Y. 1994. Grafting immortalized neurons to the CNS. *Curr. Opin. Neurobiol.* 4:742–751.
20. Snyder, E. Y. and Fisher, L. J. 1996. Gene therapy for neurologic diseases. *Curr. Opin. in Pediatr.* 8:558–568.
21. Gage, F. H. 1998. Cell therapy, *Nature* 392 (supp): 18–24.

22. Verma, I. M. and Somia, N. 1997. Gene therapy: promises, problems, and prospect, *Nature* 389:239–242.
23. Reynolds, B. A. and Weiss, S. 1996. Clonal & population anayses demonstrate that an EGF-responsive mammalian embryonic CNS precursor is a stem cell, *Develop. Biol.* 175:1–13.
24. Qian, X., Davis, A. A., Goderie, S. K., and Temple, S. 1997. FGF2 concentration regulated the generation of neurons and glia from multipotent cortical stem cells. *Neuron* 18:81–93.
25. Kilpatrick, T. and Bartlett, P. F. 1993. Cloning and growth of multipotenital neural precursors: requirements for proliferation & differentiation. *Neuron* 10:255–265.
26. Gritti, A., Parati, E. A., Cova, L., Frolichsthal, P., Galli, R., Wanke, E., Faravelli, L., Morassutti, D. J., Roisen, F., Nickel, D. D., and Vescovi, A. L. 1996. Multipotential stem cells from the adult mouse brain proliferate and self-renew in response to basic fibroblast growth factor, *J. Neurosci.* 16(3):1091–1100.
27. Gensburger, C., Laboaurdette, G., and Sensenbrenner, M. 1987. Brain basic fibroblast growth factor stimulates the proliferation of rat neuronal precursor cells in vitro. FEBS Lett 217:1–5.
28. Ryder, E. F., Snyder, E. Y., and Cepko, C. L. 1990. Establishment and characterization of multipotent neural cell lines using retrovirus vector mediated oncogene transfer, *J. Neurobiol.* 21:356–375.
29. Snyder, E. Y., Taylor, R. M., and Wolfe, J. H. 1995. Neural progenitor cell engraftment corrects lysosomal storage throughout the MPS VII mouse brain. *Nature* 374:367–370.
30. Lacorazza, H. D., Flax, J. D., Snyder, E. Y., and Jendoubi, M. 1996. Expression of human b-hexosaminidase α-subunit gene (the gene defect of Tay-Sachs disease) in mouse brains upon engraftment of transduced progenitor cells, *Nature Med.* 4:424–429.
31. Rosario, C. M., Yandaya, B. D., Kosaras, B., Zurakowsld, D. Sidman, R. L., and Snyder, E. Y. 1997. Differentation of engrafted multipotent neural progenitors towards replacement of missing granule neurons in meander tail cerebellum may help determine the locus of mutant gene action *Development* 124:4213–4224.
32. Snyder, E. Y., Yoon, C. H., Flax, J. D., and Macklis, J. D. 1997. Multipotent neural progenitors can differentiate toward replacement of neurons undergoing targeted apoptotic degeneration in adult mouse neocortex, *Proc Natl Acad Sci USA* 94:11645–11650.
33. Suhonen, J. O., Peterson, D. A., Ray, J., Gage, F. H. 1996. Differentiation of adult hippocampus-derived progenitors into olfactory neurons in vivo. *Nature* 383:624627.
34. Kitchens, D. L., Snyder, E. Y., and Gottlieb, D. I. 1994. bFGF & EGF are mitogens for immortalized neural progenitors. *J. Neurobiol.* 25:797–807.
35. Komblum, H. I., Raymon, H. K., Morrison, R. S., Cavanaugh, K. P., Bradshaw, R. A., and Leslie, F. M. 1990. Epidermal growth factor and basic fibroblast growth factor: effects on an overlapping population of neocortical neurons in vitro. *Brain Res.* 535:255–263.
36. Birren, S. J., Verdi, J. M., and Anderson, D. J. 1992. Membrane depolarization induces pl40trk and NGF responsiveness, but not p75LNGFR, in MAH cells, *Science* 257:395–397.
37. Johe, K. K, Hazel, T. G., Muller, T., Dugich-Djordjevic, M. M., and McKay, R. D. G. 1996. Single factors direct the differentiation of stem cells from the fetal and adult central nervous system. *Genes Dev.*, 10:3129–3140.
38. Snyder, E. Y. and Wolfe, J. H. 1996. CNS cell transplantation: a novel therapy for storage diseases? *Current Opin. in Neurol.* 9:126–136.
39. Yamanaka, S., Johnson, M. D., Grinberg, A., Westphal, H., Crawley, J. N., Taniike, M., Suzuki, K., and Proia, R. L. 1994. Targeted disruption of the HexA gene results in mice with biochemical and pathologic features of Tay-Sachs disease, Proc Natl Acad Sci USA 91:9975–9979.
40. Fishell, G. 1995. Striatal precursors adopt cortical identities in response to local cues. *Development* 121:803–812.
41. Campell, K., Olsson, M., and Bjorklund, A. 1995. Regional incorporation and site-specific differentiation of strail precursors transplanted to the embryonic forebrain ventricle. *Neuron* 15:1259–1273.
42. Sidman, R. L., Miale, I. L., and Feder, N. 1959. Cell proliferation and migration in the primitive ependymal zone: an autoradiographic study of histogenesis in the nervous system, *Exp. Neurol.* 1:322–333.
43. Lois, C,. Garcia-Verdugo, J.-M., and Alvarez-Buylla, A. 1996. Chain migration of neuronal precursors, *Science* 271:978–981.
44. Goldman, S. A. and Luskin, M. B. 1998. Strategies utilized by migrating neurons of the postnatal vertebrate forebrain, *Trends Neurosci.* 21:107–114.
45. Svendsen, C. N., Caldwell, M. A., Shen, J., ter Borg, M. G., Rosser, A. E., Tyers, P., Karmiol, S., and Dunnet, S. B. 1997. Long-term survival of human central nervous system progenitor cells transplanted into a rat model of Parkinson's disease, *Exp. Neurol.* 148:135–146.
46. Sabaate, O., Horellou, P., Vigne, E., Colin, P., Perricaudaet, M., Buc-Caron, M.-H., and Mallet, J., 1995. Transplantation to the rat brain of human neural progenitors that were genetically modified using adenovirus. *Nature Genetics* 9:256–260.
47. Hamre, K. M. and Goldowitz, D. 1997. Meander tail acts intrinsic to granule cell precursors to disrupt cerebellar development: analysis of meander tail chimeric mice, *Development* 124:4201–4212.
48. Gross, R. E., Mehler, M. F., Mabie, P. C., Xang, Z., Santschi, L., and Kessler, J. A. 1996. Bone morphogenetic proteins promote astroglial lineage commitment by mammalian subventricular zone progenitor cells, *Neuron* 17:595–606.
49. Borlongan, C. V., Tajima, Y., Trojanowski, J. Q., Lee, V. M., and Sanberg, P. R. 1998. Transplantation of cryopreserved human embryonal carcinoma-derived neurons (NT2N cells) promotes functional recovery in ischemic rats. *Exp. Neurol.* 149(2):310–21.
50. Sah, D. W. Y., Ray, J., and Gage, F. H. 1997. Bipotent progenitor cell lines from the human CNS, *Nature Biotech.* 15:574–580.
51. Brustle, O., Karram, Choudhary, K., Huttner, A., Murray., Dubois-Dalcq, M., and McKay, R. D. G. Chimeric brains generated by intraventricular transplantation of fetal human brain cells into embryonic rats (co-submitted, *Nature Biotech.*).
52. Vescovi, A. L., Gritti, A., Galli, R., Wanke, E., Frolichsthal-Schoeller, P., Reynolds B A, Cova L, Arcellana-Panlilio M, Mudrick-Dunnon L, Colombo A, Parati E A, Isolation of multipotential stem cells from the embryonic human CNS and establishment of transplantable human neural stem cell lines by epigenetic stimulation (co-submitted, *Nature Biotech.*).

53. Leone, G., DeGregori, J., Sears, R., Jakoi, L., Nevins, J. R. 1997. Myc and Ras collaborate in inducing accumuation of active cyclin E/Cdk2 and E2F, *Nature* 387:422–426.

54. Markowitz, D., Goff, S., snf Bank, A. 1988. Construction and use of a safe and efficient amphotropic packaging cell line, *Virology* 167:400–406.

55. Moretto, G., Xu, R. Y., Walker, D. G. and Kim, S. U. 1994. Co-expression of mRNA for neurotrophic factors in human neurons and glial cells in culture, *J Neuropath. Exp. Neurol.* 53:78–85.

What we claim is:

1. A clone of genetically modified human neural stem cells stably maintained in-vitro as an individual and distinct cell line suitable for on-demand implantation in-vivo into a living host subject, said clone comprising:

multiple primordial human neural stem cells which
   (i) originate from and are the descendant stem cells of a single, genetically modified, human neural stem cell;
   (ii) remain uncommitted and undifferentiated while passaged in-vitro as a mitotic, self-renewing cell line;
   (iii) are implantable in-vivo as uncommitted cells;
   (iv) optionally migrate in-vivo after implantation from the implantation site to other anatomic sites for integration within the nervous system of the living host subject;
   (v) integrate in-situ after implantation into the parenchymal tissues at a local anatomic site in the living host subject;
   (vi) differentiate in-situ after integration into at least one fundamental cell type selected from the group consisting of neurons, oligodendroglia and astroglia; and
   (vii) have the same genetically modified human genomic DNA in common, said DNA having been genetically modified to include a viral vector carrying at least one DNA segment comprised of an exogenous gene coding for a specific protein.

2. A clone of genetically modified human neural stem cell progeny stably maintained in-vitro as an individual and distinct cell line suitable for on-demand implantation in-vivo into a living host subject, said clone comprising:

a plurality of multipotent living progeny cells which
   (i) originate from and are the descendent progeny of a single, genetically modified, human neural stem cell ancestor;
   (ii) remain undifferentiated while passaged in-vitro as mitotic cells;
   (iii) are implantable in-vivo as undifferentiated cells;
   (iv) optionally migrate in-vivo after implantation from the implantation site to other anatomic sites for integration within the nervous system of the living host subject;
   (v) integrate in-situ after implantation into the parenchymal tissues at a local anatomic site in the living host subject;
   (vi) differentiate in-situ after integration into at least one fundamental cell type selected from the group consisting of neurons, oligodendroglia, and astroglia; and
   (vii) have the same genetically modified human genomic DNA in common, said human genomic DNA being genetically modified to include a viral vector carrying at least one DNA segment comprised of an exogenous gene coding for a specific protein.

3. The clone of cells as recited in claim 1 or 2 wherein said viral vector is an amphotrophic retroviral viral vector.

4. The clone of cells as recited in claim 1 or 2 wherein said viral vector includes an exogenous vmyc DNA sequence wherein:
   (i) said vmyc DNA sequence is highly expressed in-vitro causing said human neural stem cell to be in a proliferative cell cycle and rapidly proliferate while maintained in-vitro; and
   (ii) the expression of said vmyc DNA sequence becomes controlled and is down-regulated after cell implantation in-vivo by the constituent tissues of the living host subject such that the rate of in-vivo cell proliferation ceases.

* * * * *